(12) United States Patent
Peter

(10) Patent No.: US 6,203,197 B1
(45) Date of Patent: Mar. 20, 2001

(54) X-RAY APPARATUS WITH ELEMENTS FOR AUTOMATICALLY PRECISELY POSITIONING COMPONENTS RELATIVE TO ONE ANOTHER DURING ASSEMBLY

(75) Inventor: Fritz Peter, Spardorf (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/363,734

(22) Filed: Jul. 30, 1999

(30) Foreign Application Priority Data

Jul. 30, 1998 (DE) .............................. 198 34 457

(51) Int. Cl.$^7$ ...................................... A61B 6/00
(52) U.S. Cl. ................ 378/205; 378/19; 378/20
(58) Field of Search ................ 378/205, 19, 20, 378/193, 196, 197, 189, 207, 4

(56) References Cited

U.S. PATENT DOCUMENTS

| 4,187,429 | 2/1980 | Tomita et al. . | |
| 4,338,521 | * 7/1982 | Shaw et al. | 378/19 |
| 4,991,190 | * 2/1991 | Mori | 378/9 |
| 5,020,089 | 5/1991 | Cramer et al. . | |
| 5,469,429 | * 11/1995 | Yamazaki et al. | 378/19 |
| 5,473,657 | 12/1995 | McKenna . | |

OTHER PUBLICATIONS

Patents Abstracts of Japan, E–1067, May 14, 1991, vol. 15/No.187, for Japanese Application No. 64–182288.

* cited by examiner

Primary Examiner—David P. Porta
(74) Attorney, Agent, or Firm—Schiff Hardin & Waite

(57) ABSTRACT

An x-ray apparatus has a mounting member, an x-ray source carrier arranged at the mounting member with an x-ray source arranged therein and an x-ray detector carrier with an x-ray detector arranged therein, wherein the x-ray source must be exactly adjusted relative to the x-ray detector within an overall tolerance for a proper operation of the x-ray arrangement. A source tolerance, a detector tolerance, a source carrier tolerance and a detector carrier tolerance are provided, with the sum of these tolerances of the assemblies being no larger than the overall tolerance.

6 Claims, 3 Drawing Sheets

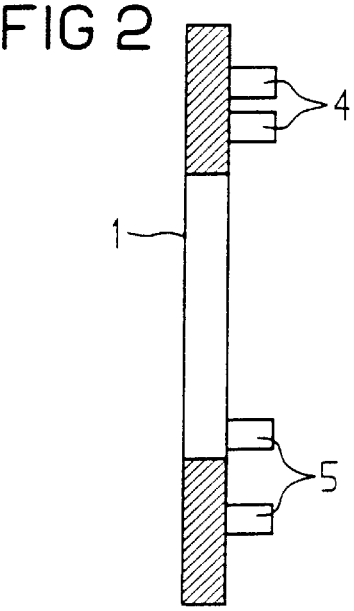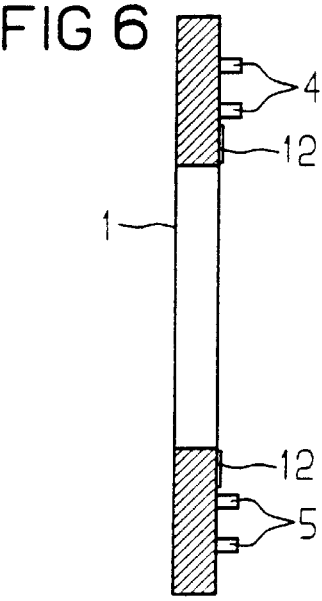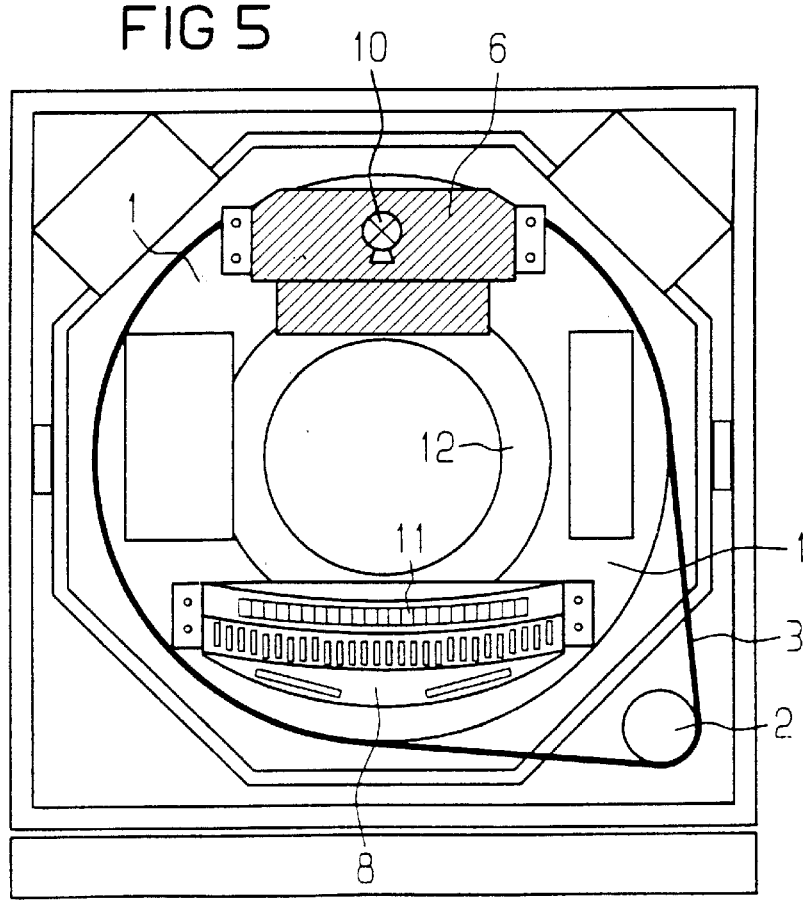

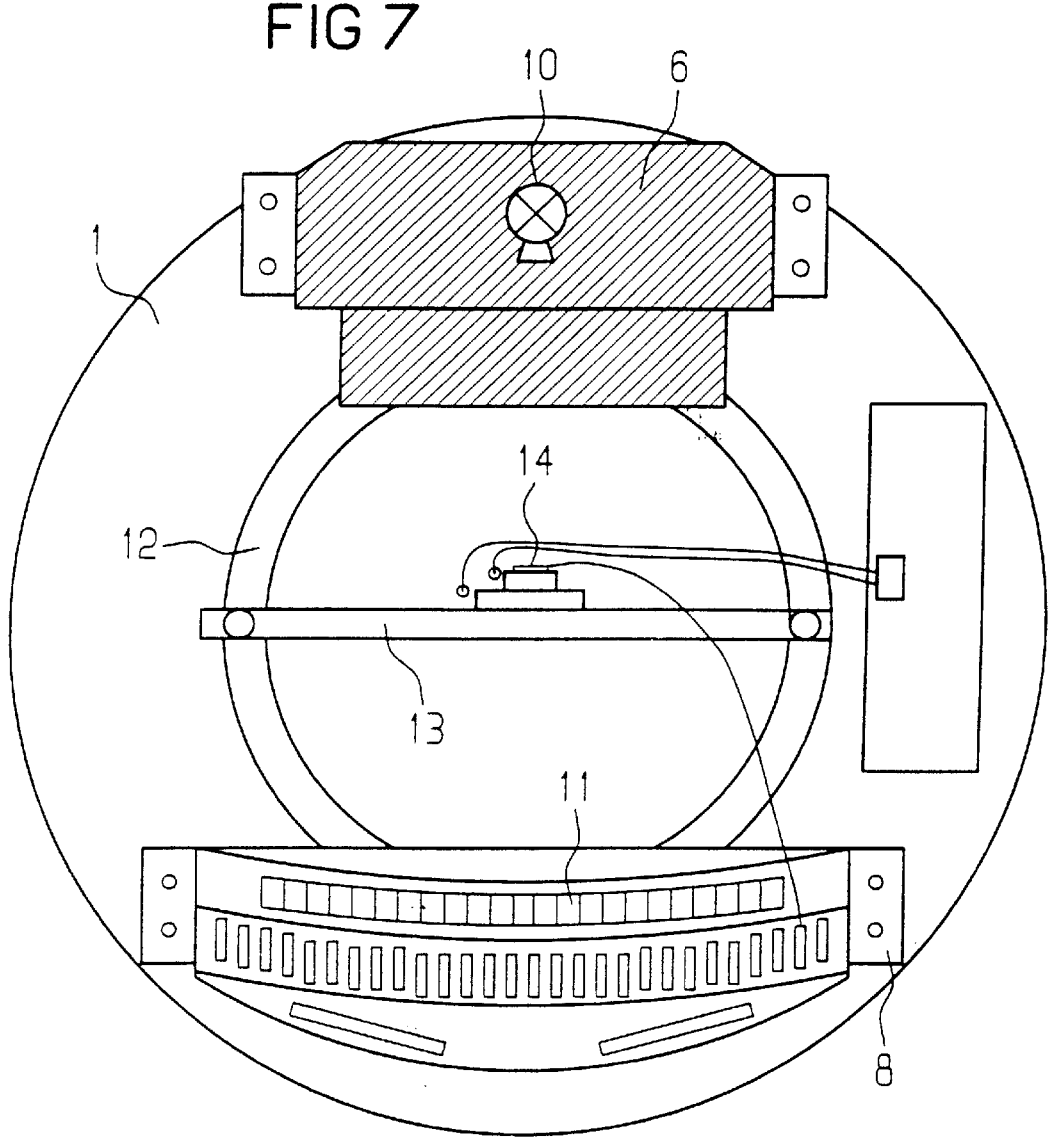

X-RAY APPARATUS WITH ELEMENTS FOR AUTOMATICALLY PRECISELY POSITIONING COMPONENTS RELATIVE TO ONE ANOTHER DURING ASSEMBLY

BACKGROUND OF THE INVENTION

1. Field of the Invention

The present invention is directed to an x-ray apparatus of the type having a mounting member, an x-ray source arranged at the mounting member and an x-ray detector arranged at the mounting member, wherein the x-ray source must be exactly adjusted relative to the x-ray detector within an overall tolerance for a proper operation of the x-ray apparatus.

2. Description of the Prior Art

X-ray arrangements of the above general type are disclosed, for example, by U.S. Pat. Nos. 5,020,089 and 5,473,657 and 4,187,429 and in Patent Abstracts of Japan, 1991, JP 3-46 797 A. After mounting the individual components, an adjustment of the x-ray source and the x-ray detector relative to one another, by a displacement of these components relative to one another, is required. The adjustment can thereby ensue manually or automatically.

Such an adjustment is time-consuming and expensive and also is complicated. Moreover, the adjustment can only be undertaken by qualified personnel. There is also the possibility of radiation exposure to the personnel.

SUMMARY OF THE INVENTION

An object of the present invention is to provide x-ray arrangement such that the disadvantages of the prior art are avoided.

This object is inventively achieved in an x-ray arrangement having a mounting member, an x-ray source carrier arranged at the mounting member with an x-ray source arranged therein and an x-ray detector carrier having an x-ray detector arranged therein, wherein the x-ray source must be adjusted exactly with respect to the x-ray detector within an overall tolerance for a proper operation of the x-ray arrangement, and wherein the x-ray source and the x-ray source carrier have interacting source adjustment elements that automatically adjust the x-ray source exactly relative to the x-ray source carrier within a source tolerance during assembly of the x-ray source carrier, and wherein the x-ray detector and the x-ray detector carrier have interacting detector adjustment elements that automatically adjust the x-ray detector exactly relative to the x-ray detector carrier within a detector tolerance during assembly of the x-ray detector carrier, and wherein the x-ray source carrier and the mounting member have interacting source carrier adjustment elements that automatically adjust the x-ray source carrier exactly relative to the mounting member within a source carrier tolerance during assembly of the x-ray source carrier at the mounting member, and wherein the x-ray detector carrier and the mounting member have interacting detector adjustment elements that automatically adjust the x-ray detector carrier exactly relative to the mounting member within a detector carrier tolerance during assembly of the x-ray detector carrier at the mounting member, and wherein the sum of the source tolerance, detector tolerance, source carrier tolerance and detector carrier tolerance is no longer than the overall tolerance.

In the inventive assembly, adherence to the overall tolerance is necessarily assured without requiring an adjustment by displacement of the components relative to one another.

Test measurements are required for checking the adjustment. To this end, test samples must be introduced into the beam path at defined locations. The x-ray arrangement therefore preferably has the mounting member and a test carrier arranged at the mounting member with interacting test carrier adjustment elements that adjust the text carrier exactly relative to the mounting member within a test carrier tolerance when the test carrier is mounted at the mounting member, and the test carrier and a test sample arranged at the test carrier have interacting sample adjustment elements that adjust the test sample exactly relative to the sample carrier within a sample tolerance when the test sample is mounted at the sample carrier.

The respectively interacting adjustment elements can, for example, be fashioned as stop elements, as adjustment bores and adjustment pegs, or as adjustment surfaces. Given fashioning as adjustment bores and adjustment pegs, the adjustment pegs are preferably conically fashioned at least in portion thereof.

DESCRIPTION OF THE DRAWINGS

FIG. 2 is a side view of a mounting member for the inventive x-ray apparatus.

FIG. 5 is a cross-section through a further embodiment of a computed tomography apparatus having an x-ray apparatus according to the invention.

FIG. 6 is a side view of a further embodiment of a mounting member for the inventive x-ray apparatus.

FIG. 7 shows a mounting member with x-ray components mounted thereon.

DESCRIPTION OF THE PREFERRED EMBODIMENTS

Figure 1:
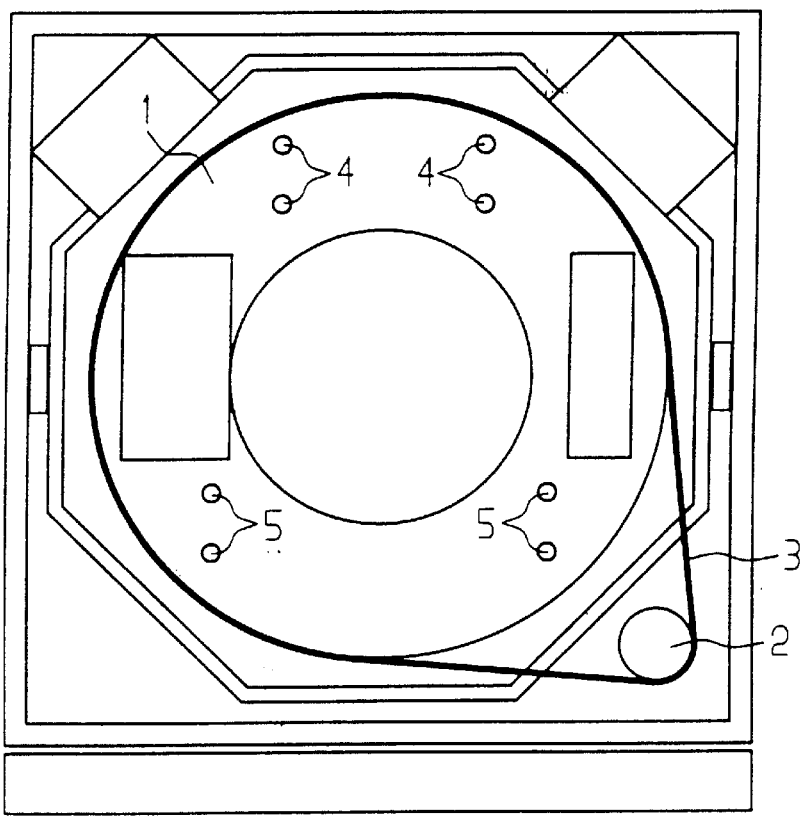
FIG. 1 is a cross-section through a computed tomography apparatus having an x-ray apparatus according to the invention.

As shown in FIG. 1, a computed tomography apparatus as an example of an inventive x-ray apparatus has, among other things, a mounting member 1 that, for example, is rotatable with a motor 2 and a drive belt 3. Alternatively, the mounting member 1 could, for example, be driven via gears or a friction wheel. The mounting member 1 has source carrier adjustment elements 4 and detector carrier adjustment elements 5.

As shown in FIG. 2, the source carrier adjustment elements 4 and the detector carrier adjustment elements 5 of the mounting member 1 are fashioned as cylindrical adjustment pegs 4, 5. The adjustment pegs 4, can be conically fashioned, at least in a front portion thereof. Alternatively, the source carrier adjustment elements 4 and/or the detector carrier adjustment elements 5 of the mounting member 1 can be formed as stop elements or as adjustment surfaces.

Figure 3:
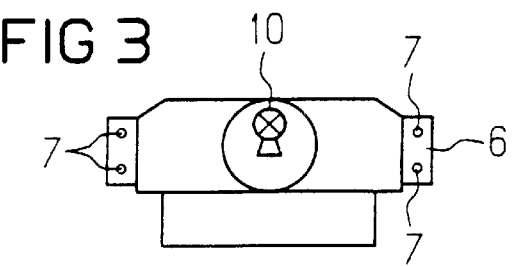
FIG. 3 shows an x-ray source carrier of the inventive x-ray apparatus.

An x-ray source carrier 6 shown in FIG. 3 similarly has source carrier adjustment elements 7. In the exemplary embodiment, they are fashioned as adjustment bores. The source carrier adjustment elements 7 of the x-ray source carrier 6 interact with the source carrier adjustment elements 4 of the mounting member 1. Due to the interaction of the source carrier adjustment elements 4, 7, the x-ray source carrier 6 is automatically exactly adjusted relative to the mounting member 1 within a source carrier tolerance when mounting the x-ray source carrier 6 at the mounting member 1.

Figure 4:
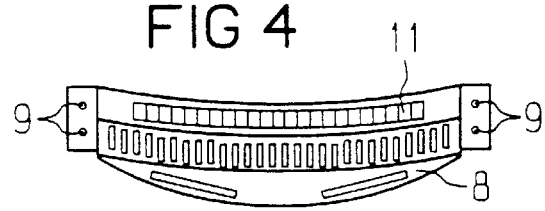
FIG. 4 shows an x-ray detector carrier of the inventive x-ray apparatus.

An x-ray detector carrier H shown in FIG. 4 likewise has detector carrier adjustment elements 9 that, in the exemplary embodiment, are likewise fashioned as adjustment bores. The detector carrier adjustment elements 9 of the x-ray detector carrier 8 interact with the detector carrier adjustment elements 5 of the mounting member 1. As a result, the x-ray detector carrier 8 is automatically precisely adjusted relative to the mounting member 1 within a detector carrier tolerance when the x-ray detector carrier 8 is mounted at the mounting member 1.

An x-ray source 10 is attached in the x-ray source carrier 6. The x-ray source 10 as well as the x-ray source carrier 6 have interacting source adjustment elements that are constructed similar to the source carrier adjustment elements 4, 7 or similar to the detector carrier adjustment elements 5, 9. Due to the interaction of the source adjustment elements, the x-ray source 10 is automatically precisely adjusted relative to the x-ray source carrier 6 within a source tolerance when the x-ray source carrier 6 is assembled. Diaphragms, etc., which are not shown for clarity, can be optionally allocated to the x-ray source carrier 6 or to the x-ray source 10. These also are automatically co-adjusted when the x-ray source carrier 6 is assembled.

An x-ray detector 11 is likewise arranged inside the x-ray detector carrier 8. The x-ray detector 11 and the x-ray detector carrier 8 have interacting detector adjustment elements. Due to the interaction of the detector adjustment elements, the x-ray detector 11 is necessarily exactly adjusted relative to the x-ray detector carrier within a detector tolerance when the x-ray detector carrier 8 is assembled. The above description of the diaphragms of the x-ray source carrier 6 also apply by analogy to diaphragms, that are not shown for clarity.

For a proper operation of the computed tomography apparatus, the x-ray source 10 must be exactly adjusted relative to the x-ray detector 11 within an overall tolerance. Due to a suitable selection of source tolerance, detector tolerance, source carrier tolerance and detector carrier tolerance, the sum of these tolerances is no larger than the overall tolerance. By simply assembling x-ray source carrier 6 and x-ray detector carrier 8 as well as subsequent mounting of the x-ray source carrier 6 and the x-ray detector carrier 8 at the mounting member 1, the x-ray source 10 is automatically exactly adjusted relative to the x-ray detector 11 within the overall tolerance of necessity. Fine adjustment is no longer required.

FIG. 5 shows a further computed tomography apparatus wherein the x-ray source carrier 6 and the x-ray detector carrier 8 are already secured to the mounting member 1. As a supplement, the mounting member has sample carrier adjustment elements 12. The sample carrier adjustment elements 12 are fashioned as stop element according to FIG. 6. Since, in this case, a one-dimensional adjustment is adequate, the sample carrier adjustment elements 12 alternatively can be fashioned as adjustment surfaces.

A sample carrier 13 that can be seen according to FIG. 7 is arranged at the mounting member 1, and has sample carrier adjustment elements interacting with these sample carrier adjustment elements 12. As a result, the sample carrier 13 can be automatically adjusted exactly relative to the mounting member 1 within a sample carrier tolerance when mounted at the mounting member 1.

The sample carrier 13 and a test sample 14 arranged at the sample carrier 13 likewise have interacting sample adjustment elements. As a result, the test sample 14 is automatically exactly adjustable relative to the sample carrier 13 within a sample tolerance when the test sample 14 is mounted at the sampler carrier 13. The sum of source tolerance, detector tolerance, source carrier tolerance, detector carrier tolerance, sample carrier tolerance and sample tolerance likewise are less than the overall tolerance.

Although modifications and changes may be suggested by those skilled in the art, it is the intention of the inventor to embody within the patent warranted hereon all changes and modifications as reasonably and properly come within the scope of his contribution to the art.

I claim as my invention:

1. An x-ray apparatus comprising a mounting member, an x-ray source carrier arranged at the mounting member, an x-ray source arranged therein at the mounting member and an x-ray detector carrier, an x-ray detector arranged at the detector carrier, said x-ray source requiring exact adjustment relative to the x-ray detector within an overall tolerance said x-ray source and the x-ray source carrier having interacting first source adjustment elements that automatically exactly adjust the x-ray source relative to the x-ray source carrier within a source tolerance during assembly of the x-ray source carrier, said x-ray detector and the x-ray detector carrier having interacting first detector adjustment elements that automatically exactly adjust the x-ray detector relative to the x-ray detector carrier within a detector tolerance during assembly of the x-ray detector, said x-ray source carrier and the mounting member having interacting second source carrier adjustment elements that automatically exactly adjust the x-ray source carrier relative to the mounting member within a source carrier tolerance when the x-ray source carrier is mounted at the mounting member, said x-ray detector carrier and the mounting member having interacting second detector carrier adjustment elements that automatically exactly adjust the x-ray detector carrier relative to the mounting member within a detector carrier tolerance when the x-ray detector carrier is mounted at the mounting member, and a sum of the source tolerance, the detector tolerance, the source carrier tolerance and the detector carrier tolerance being no larger than the overall tolerance.

2. An x-ray apparatus according to claim 1, further comprising a test sample and a sample carrier arranged of the mounting member, the mounting member and the sample carrier having interacting sample carrier adjustment elements that automatically exactly adjust the sample carrier relative to the mounting member within a sample carrier tolerance when the sample carrier is mounted at the mounting member, the sample carrier and the test sample arranged at the sample carrier have interacting sample adjustment elements that automatically exactly adjust the test sample relative to the sample carrier within a sample tolerance when the test sample is mounted at the sample carrier.

3. An x-ray apparatus according to claim 1, wherein the interacting adjustment elements comprise stop elements.

4. An x-ray apparatus according to claim 1, wherein the interacting adjustment means comprises adjustment surfaces.

5. An x-ray apparatus according to claim 1, wherein the interacting adjustment elements comprise adjustment bores and adjustment pegs.

6. An x-ray apparatus according to claim 5, wherein the adjustment pegs are conical at least in a portion thereof.

* * * * *